(12) United States Patent
Lam et al.

(10) Patent No.: US 6,329,187 B1
(45) Date of Patent: Dec. 11, 2001

(54) ENDOGLUCANASES

(75) Inventors: David E. Lam, Harbor City; Eric J. Mathur, Carlsbad, both of CA (US)

(73) Assignee: Diversa Corporation, San Diego, CA (US)

( * ) Notice: Subject to any disclaimer, the term of this patent is extended or adjusted under 35 U.S.C. 154(b) by 0 days.

(21) Appl. No.: 09/430,669

(22) Filed: Oct. 28, 1999

Related U.S. Application Data

(62) Division of application No. 09/066,544, filed on Apr. 24, 1998, now Pat. No. 6,001,984, which is a continuation of application No. 08/651,572, filed on May 22, 1996, now Pat. No. 5,789,228.

(51) Int. Cl.$^7$ ............................... C12N 9/00; C12N 9/24; C12N 9/42

(52) U.S. Cl. ...................... 435/209; 435/183; 435/200; 435/220; 536/23.2

(58) Field of Search .................................. 435/183, 209, 435/220; 536/23.2

(56) References Cited

U.S. PATENT DOCUMENTS

| | | | |
|---|---|---|---|
| 5,475,101 | * | 12/1995 | Ward et al. ..................... 536/23.74 |
| 5,536,655 | * | 7/1996 | Thomas et al. ..................... 435/209 |
| 5,643,791 | * | 7/1997 | Warren et al. ..................... 435/252.33 |
| 5,723,328 | * | 3/1998 | Dalboege et al. ..................... 435/209 |
| 5,789,228 | * | 8/1998 | Lam et al. ..................... 435/209 |
| 5,817,499 | * | 10/1998 | Dalboge et al. ..................... 435/200 |

FOREIGN PATENT DOCUMENTS

| | | |
|---|---|---|
| 42 04 476 | 8/1992 | (DE). |
| 0 606 008 | 7/1994 | (EP). |
| 0 648 843 | 4/1995 | (EP). |
| 0 687 732 | 12/1995 | (EP). |
| 02 276578 | 11/1990 | (JP). |
| 09 173077 | 7/1997 | (JP). |
| WO9502043 * | 1/1995 | (WO). |
| WO 95 20047 | 7/1995 | (WO). |
| WO9602551A1 * | 2/1996 | (WO). |
| WO 97 20918 | 6/1997 | (WO). |
| WO 97 25417 | 7/1997 | (WO). |
| WO 98 24799 | 6/1998 | (WO). |
| WO 98 33895 | 8/1998 | (WO). |

OTHER PUBLICATIONS

Matthews et al., Analytical Biochemistry 169 : 1–25 (1988).*

Baba, T. et al.. "Identification and Characterization of Clustered Genes for Thermostable Xylan–Degrading Enzymes, Beta–Xylosidase and Xylanase, of Bacillus Stearothermophilus 21", *Applied and Environmental Microbiology*, U.S. Washington, D.C., vol. 60, No. 7, Jul. 1, 1994 (pp. 2252–2258).

Dean, R.C.. "Mechanisms of Wood Digestion in the Shipworm Bankia–Gouldi Enzyme Degradation of Celluloses Hemi Celluloses and Wood Cell Walls", Database Accession No. PREV198069003408 XP002159358 (Abstract) and Biological Bulletin (Woods Hole), vol. 155, No. 2, 1978 (pp. 297–316).

Lao et al., "DNA Sequences of Three Beta–1,4–Endoglucanase Genes From Thermomonospora Fusca", XP002094152 *Journal of Bacteriology*, vol. 173, Jun. 1, 1991 (pp. 3397–3407).

Lin, E.S. et al., "Thermomonospora Fusca Beta–1,4–Endoglucanaseprecursor (E4) Gene, Complete CDS", Accession L20093, XP002159359 Jul. 8, 1993 (pp. 70–469).

Jung et al., "DNA Sequences and Expression in Streptomyces Lividans of an Exoglucanase Gene and an Endoglucanase Gene From Thermomonospora Fusca", Accession P26221 XP002159360 May 1, 1992, pp. 6–864).

Milward–Sadler Sarah J. et al., Novel Cellulose–Binding Domains, NodB Homologues and Conserved Modular Architecture in Xylanases from the Aerobic Soil Bacteria Pseudomonas Fluorescens Subsp. Cellulosa and Cellvibrio Mixtus, *Biochemical Journal*, vol. 312, No. 1, 1995, (pp. 39–48).

Clarke, J.H., "P. Fluorescens SSP. Cellulosa Gene for Endo–Beta–1,4–Xylanase", Accession Z48928, XP002159361, Mar. 30, 1995 (pp. 982–1604).

Millward–Sadler S.J. et al., "Endo–Beta–1,4–Xylanase Precursor (EC 3.2.1.8) (Endo–1,4–Beta–Xylanase)" Accession No. Q59765 XP002159362 Nov. 1, 1996 (pp. 298–580).

Hall J. et al., "The Non–Catalytic Cellulose–Binding Domain of a Novel Cellulase From Pseudomonas Fluorescens Subsp. Cellulose is Important for the Efficient Hydrolysis of Avicel", *Biochemical Journal*, G.B., Portland Press, London, vol. 309, No. Part 3, Aug. 1, 1995, (pp. 749–756).

Hall, J. et al., "P. Fluorescens Cele Gen", Accession No. X86798, XP002159363, May 11, 1995 (pp. 1159–1831).

Hall, J. et al., "Endo–1,4–Beta–Glucanase (EC 3.2.1.4) (Cellulase) (Endoglucanase) (Carboxymethyl Cellulase)", Accession No. Q59665, XP002159364 Nov. 1, 1996 (pp. 6–565).

Waterbury J.B. et al., "A Cellulolytic Nitrogen Fixing Bacterium Cultured from the Gland of Deshayes in Shipworms Bivalvia Teredinidae", Database Accession No. PREV198477059970, XP002159365 (Abstract) and Science (Washington, D.C.) vol. 221, No. 4618, 1983 (pp. 1401–1403).

(List continued on next page.)

Primary Examiner—Rebecca E. Prouty
Assistant Examiner—Manjunath N. Rao
(74) *Attorney, Agent, or Firm*—Gray Cary Ware & Freidenrich LLP; Lisa A. Haile

(57) ABSTRACT

A purified thermostable enzyme is derived from the archael bacterium AEPII1a. The enzyme has a molecular weight of about 60.9 kilodaltons and has cellulase activity. The enzyme can be produced from native or recombinant host cells and can be used to aid in the digestion of cellulose where desired.

8 Claims, 2 Drawing Sheets

OTHER PUBLICATIONS

Watanabe et al., "Proline Residues Responsible for Thermostability Occur with High Frequency in the Loop Regions of an Extremely Thermostable Oligo–1 6–Glucosidase from Bacillus–Thermoglucosidasius KP 1006", *Journal of Biological Chemistry*, vol. 266, No. 36, 1991 (pp. 24287–24294).

King Michael et al., "Thermostable Alpha–Galactosidase from Thermotoga Neapolitana: Cloning Sequencing and Expression", *FEMS Microbiology Letters*, vol. 163, No. 1, Jun. 1, 1998 (pp. 37–42).

King, M.R. et al., "Alpha–1, 6–Galactosidase (EC 3.2.1.22)", Accession No. Q9R7H1, XP002159366 (May 1, 2000) (pp. 68–618).

King, M.R. et al., "Thermotoga Neapolitana Alpha–1,6–Galactosidase (ag1 A) Gene, Complete CDS", Accession No. AF011400, XP002159367, Jun. 19, 1998, (pp. 1–1716).

Moore, J.B. et a., "Thermotoga Maritima Beta–Galactosidase (LACZ) Gene, Complete CDS, and ATP–Dependent Oligopeptide Transport Protein D Gene, Partial CDS", Accession No. UO8186, XP002159368, Apr. 18, 1994, (pp. 2–962).

Parker et al., "Thermotoga Neopolitana manB Gene", Accession No. Y17981, XP002159369, Sep. 30, 1999.

Hayden et al., "Sec–Independent Protein Translocase Protein Tate", Accession No. P25895, XP002159370, May 1, 1992 (pp. 5–59).

Voorhorst Wilfried G.B. et al., "Characterization of the Celb Gene Coding for Beta–Glucosidase from the Hyperthermophilic Archaeon Pyrococcus Furiosus and its Expression and Site–Directed Mutation in *Escherichia coli*", *Journal of Bacteriology*, vol. 177, No. 24, 1994, (pp. 7105–7111).

Voorhorst W.G. et a., "Pyrococcus Furiosus Beta–Glucosidase (celB) Gene, Complete CDS; ADH–1AM Operon, Complete Sequence; Biotin Ligase Bira Homolog (Bira) Gene, Complete CDS; and 2–Posphoglycerate Kinase (PGK) Gene, Partial CDS", Accession No. AFO13169, XP002159371 Jul. 7, 1998 (pp. 1624–729).

Voorhorst et al., "Beta–Glucosidase", Accession No. Q51723, XP002159372, Nov. 1, 1996 (pp. 1–478).

Tachibana Yoshihisa et al., "Cloning and Expression of the Alpha–Amylase Gene from the Hyperthermophilic Archaeon Pyrococcus SP. KOD1, and Characterization of the Enzyme", *Journal of Fermentation and Bioengineering*, vol. 82, No. 3, 1996 (pp. 224–232).

Nelson K.E. et al., "Thermotoga Maritima Section 125 of 136 of the Complete Genome", Accession No. AE001813, XP002159373, Jun. 4, 1999.

Wang W et al., "Nucleotide Sequence of the celA Gene Encoding a Cellodesctrinase of Ruminococcus Flavefaciens Formal Drawings–1", Accession No. P16169, XP00215374, Apr. 1, 1990 (pp. 17–287).

Nelson K.E. et al., "Thermotoga Maritima Section 134 of 136 of the Complete Genome", Accession No. AE001822, XP002159375, Jun. 4, 1999.

Yoshihisa et al., Alpha–Mannosidase (EC 3.2.1.24) (Alpha–D Mannoside Mannohydrolase), Accession No. P22855, XP–002159376, Aug. 1, 1991 (pp. 9–946).

Nelson, K.E. et al., "Thermotoga Maritima Section 6 of 136 of the Complete Genome", Accession No. AE001694, Xp–002159377, Jun. 4, 1999 (pp. 4969–8305).

Yernool D.A. et al., "Thermotoga Neapolitana Mannosidase (manA), Xylosidase (xloA), and Acetyl Xylan Esterase (axeA) Genes, Complete CDS", Accession No. U58632, XP002159378, Jun. 21, 1996.

Breves et al., "T–Brockii CGLF, XGLS, and CTLT Genes," Accession No. Z56279, XP002159379, Oct. 13, 1995.

Gilbert H.J., "P–Fluorescens celD Gene for 1, 4–B–D–G–lucan Glucohydrolase", Accession X65527, XP002159380, May 5, 1992.

Svitil A.L. et al., "Vibrio Harveyi Chitinase A (Chia) Gene, Complete CDS", Accession No. U81496, XP002159381, Jan. 5, 1997.

Ramesh et al., "Cellulytic Activity of 1–13 Luminous Bacteria", *Mircen Journal of Applied Microbiology and Biotechnology*, vol. 4, No. 2, 1988 (pp. 227–230).

O.N. Dakhova et al., "Cloning and Expression in *Escherichia coli* of Thermotoga Neapolitana Genes Cloning For Enzymes of Carbohydrate Substrate Degradation", *Biochemical and Biophysical Research Communications*, vol. 194, No. 3, Aug. 16, 1993, pp. 1359–1364.

\* cited by examiner

```
                9              18              27              36              45              54
ATG ATA AAC GTT GCA ACG GGA GAG GAG ACC CCA ATA CAC CTC TTT GGA GTC AAC
Met Ile Asn Val Ala Thr Gly Glu Glu Thr Pro Ile His Leu Phe Gly Val Asn 63              72              81              90              99             108
TGG TTC GGC TTT GAG ACA CCG AAC TAC GTT GTT CAC GGC CTA TGG AGT AGG AAC
Trp Phe Gly Phe Glu Thr Pro Asn Tyr Val Val His Gly Leu Trp Ser Arg Asn 117             126             135             144             153             162
TGG GAG GAC ATG CTC CTC CAG ATC AAG AGC CTT GGC TTC AAT GCG ATA AGG CTT
Trp Glu Asp Met Leu Leu Gln Ile Lys Ser Leu Gly Phe Asn Ala Ile Arg Leu 171             180             189             198             207             216
CCC TTC TGT ACC CAG TCA GTA AAA CCG GGG ACG ATG CCA ACG GCG ATT GAC TAC
Pro Phe Cys Thr Gln Ser Val Lys Pro Gly Thr Met Pro Thr Ala Ile Asp Tyr 225             234             243             252             261             270
GCC AAG AAC CCA GAC CTC CAG GGT CTT GAC AGC GTC CAG ATA ATG GAG AAA ATA
Ala Lys Asn Pro Asp Leu Gln Gly Leu Asp Ser Val Gln Ile Met Glu Lys Ile 279             288             297             306             315             324
ATC AAG AAG GCT GGA GAC CTG GGC ATA TTC GTG CTC CTC GAC TAC CAC AGA ATA
Ile Lys Lys Ala Gly Asp Leu Gly Ile Phe Val Leu Leu Asp Tyr His Arg Ile 333             342             351             360             369             378
GGA TGC AAC TTC ATA GAA CCC CTA TGG TAC ACC GAC AGC TTC TCG GAG CAG GAC
Gly Cys Asn Phe Ile Glu Pro Leu Trp Tyr Thr Asp Ser Phe Ser Glu Gln Asp 387             396             405             414             423             432
TAC ATA AAC ACC TGG GTT GAA GTC GCC CAG AGG TTC GGC AAG TAC TGG AAC GTT
Tyr Ile Asn Thr Trp Val Glu Val Ala Gln Arg Phe Gly Lys Tyr Trp Asn Val 441             450             459             468             477             486
ATC GGC GCG GAC CTG AAG AAC GAA CCC CAC AGC TCA AGC CCC GCA CCT GCC GCC
Ile Gly Ala Asp Leu Lys Asn Glu Pro His Ser Ser Ser Pro Ala Pro Ala Ala 495             504             513             522             531             540
TAC ACT GAC GGA AGT GGG GCC ACG TGG GGA ATG GGC AAC AAC GCC ACC GAC TGG
Tyr Thr Asp Gly Ser Gly Ala Thr Trp Gly Met Gly Asn Asn Ala Thr Asp Trp 549             558             567             576             585             594
AAC CTG GCG GCT GAG AGG ATA GGA AGG GCA ATT CTG GAG GTT GCC CCA CAA TGG
Asn Leu Ala Ala Glu Arg Ile Gly Arg Ala Ile Leu Glu Val Ala Pro Gln Trp 603             612             621             630             639             648
GTT ATA TTT GTT GAG GGA ACC CAG TTC ACC ACC CCC GAG ATA GAC GGT AGG TAC
Val Ile Phe Val Glu Gly Thr Gln Phe Thr Thr Pro Glu Ile Asp Gly Arg Tyr 657             666             675             684             693             702
AAG TGG GGC CAC AAC GCC TGG TGG GGC GGA AAC CTT ATG GGT GTT AGG AAG TAC
Lys Trp Gly His Asn Ala Trp Trp Gly Gly Asn Leu Met Gly Val Arg Lys Tyr 711             720             729             738             747             756
CCA GTT AAC CTG CCC AGG GAC AAG GTT GTT TAC AGC CCC CAA GTT TAC GGT TCA
Pro Val Asn Leu Pro Arg Asp Lys Val Val Tyr Ser Pro Gln Val Tyr Gly Ser 765             774             783             792             801             810
GAA GTT TAC GAC CAG CCC TAC TTT GAC CCC GGT GAG GGG TTC CCC GAC AAC CTC
Glu Val Tyr Asp Gln Pro Tyr Phe Asp Pro Gly Glu Gly Phe Pro Asp Asn Leu 819             828             837             846             855             864
CCC GAA ATA TGG TAC CAC CAC TTC GGC TAC GTA AAG CTT GAT CTC GGT TAC CCT
Pro Glu Ile Trp Tyr His His Phe Gly Tyr Val Lys Leu Asp Leu Gly Tyr Pro
```

FIG. 1A

```
        873             882             891             900             909             918
GTT GTT ATA GGT GAG TTC GGA GGC AAG TAC GGC CAT GGG GGA GAC CCG AGG GAT
Val Val Ile Gly Glu Phe Gly Gly Lys Tyr Gly His Gly Gly Asp Pro Arg Asp 927             936             945             954             963             972
GTC ACT TGG CAG AAC AAG ATA ATA GAC TGG ATG ATC CAG AAC AAA TTC TGT GAC
Val Thr Trp Gln Asn Lys Ile Ile Asp Trp Met Ile Gln Asn Lys Phe Cys Asp 981             990             999            1008            1017            1026
TTC TTC TAC TGG AGC TGG AAC CCA AAC AGC GGT GAC ACC GGT GGA ATT CTG AAG
Phe Phe Tyr Trp Ser Trp Asn Pro Asn Ser Gly Asp Thr Gly Gly Ile Leu Lys 1035            1044            1053            1062            1071            1080
GAT GAC TGG ACG ACA ATA TGG GAG GAC AAG TAC AAC AAC CTG AAG AGG CTC ATG
Asp Asp Trp Thr Thr Ile Trp Glu Asp Lys Tyr Asn Asn Leu Lys Arg Leu Met 1089            1098            1107            1116            1125            1134
GAC AGC TGT TCT GGA AAC GCC ACT GCC CCG TCC GTC CCC ACG ACA ACT ACA ACA
Asp Ser Cys Ser Gly Asn Ala Thr Ala Pro Ser Val Pro Thr Thr Thr Thr Thr 1143            1152            1161            1170            1179            1188
ACA AGC ACA CCG CCA ACG ACC ACA ACG ACT ACA ACA TCC ACT CCA ACG ACC ACT
Thr Ser Thr Pro Pro Thr Thr Thr Thr Thr Thr Thr Ser Thr Pro Thr Thr Thr 1197            1206            1215            1224            1233            1242
ACC CAG ACC CCG ACC ACC ACT ACT CCA ACT ACG ACA ACC ACC ACG ACC ACA ACT
Thr Gln Thr Pro Thr Thr Thr Thr Pro Thr Thr Thr Thr Thr Thr Thr Thr Thr 1251            1260            1269            1278            1287            1296
CCT TCA AAT AAC GTC CCA TTT GAA ATT GTG AAC GTT CTC CCG ACT AGC TCC CAG
Pro Ser Asn Asn Val Pro Phe Glu Ile Val Asn Val Leu Pro Thr Ser Ser Gln 1305            1314            1323            1332            1341            1350
TAC GAG GGA ACC AGC GTG GAG GTT GTA TGT GAT GGA ACC CAG TGT GCC TCC AGC
Tyr Glu Gly Thr Ser Val Glu Val Val Cys Asp Gly Thr Gln Cys Ala Ser Ser 1359            1368            1377            1386            1395            1404
GTT TGG GGA GCT CCG AAC CTC TGG GGA GTC GTT AAA ATC GGA AAC GCC ACC ATG
Val Trp Gly Ala Pro Asn Leu Trp Gly Val Val Lys Ile Gly Asn Ala Thr Met 1413            1422            1431            1440            1449            1458
GAC CCC AAC GTT TGG GGC TGG GAG GAC GTT TAC AAG ACT GCA CCC CAG GAC ATT
Asp Pro Asn Val Trp Gly Trp Glu Asp Val Tyr Lys Thr Ala Pro Gln Asp Ile 1467            1476            1485            1494            1503            1512
GGA ACC GGC AGC ACA AAG ATG GAG ATA AGG AAC GGG GTG CTC AAG GTT ACA AAC
Gly Thr Gly Ser Thr Lys Met Glu Ile Arg Asn Gly Val Leu Lys Val Thr Asn 1521            1530            1539            1548            1557            1566
CTC TGG AAC ATC AAC ATG CAT CCG AAG TAT AAC ACA ATG GCA TAC CCG GAG GTC
Leu Trp Asn Ile Asn Met His Pro Lys Tyr Asn Thr Met Ala Tyr Pro Glu Val 1575            1584            1593            1602            1611            1620
ATA TAC GGC GCC AAG CCT TGG GGC AAC CAG CCA ATA AAC GCT CCG AAC TTC GTG
Ile Tyr Gly Ala Lys Pro Trp Gly Asn Gln Pro Ile Asn Ala Pro Asn Phe Val 1629            1638            1647            1656
CTC CCG ATA AAG GTC TCC CAG CTT CCG AGG ATA CTT CGT TGA
Leu Pro Ile Lys Val Ser Gln Leu Pro Arg Ile Leu Arg ***
```

FIG. 1B

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 1662 NUCLEOTIDES
      (B) TYPE: NUCLEIC ACID
      (C) STRANDEDNESS: SINGLE
      (D) TOPOLOGY: LINEAR (ii) MOLECULE TYPE: DNA (xi) SEQUENCE DESCRIPTION: SEQ ID NO: 1:

```
ATG ATA AAC GTT GCA ACG GGA GAG GAG ACC CCA ATA CAC CTC TTT GGA      48
Met Ile Asn Val Ala Thr Gly Glu Glu Thr Pro Ile His Leu Phe Gly
              5                  10                  15

GTC AAC TGG TTC GGC TTT GAG ACA CCG AAC TAC GTT GTT CAC GGC CTA      96
Val Asn Trp Phe Gly Phe Glu Thr Pro Asn Tyr Val Val His Gly Leu
         20                  25                  30

TGG AGT AGG AAC TGG GAG GAC ATG CTC CTC CAG ATC AAG AGC CTT GGC     144
Trp Ser Arg Asn Trp Glu Asp Met Leu Leu Gln Ile Lys Ser Leu Gly
     35                  40                  45

TTC AAT GCG ATA AGG CTT CCC TTC TGT ACC CAG TCA GTA AAA CCG GGG     192
```

```
Phe Asn Ala Ile Arg Leu Pro Phe Cys Thr Gln Ser Val Lys Pro Gly
 50                  55                  60

ACG ATG CCA ACG GCG ATT GAC TAC GCC AAG AAC CCA GAC CTC CAG GGT        240
Thr Met Pro Thr Ala Ile Asp Tyr Ala Lys Asn Pro Asp Leu Gln Gly
 65                  70                  75                  80

CTT GAC AGC GTC CAG ATA ATG GAG AAA ATA ATC AAG AAG GCT GGA GAC        288
Leu Asp Ser Val Gln Ile Met Glu Lys Ile Ile Lys Lys Ala Gly Asp
                     85                  90                  95

CTG GGC ATA TTC GTG CTC CTC GAC TAC CAC AGA ATA GGA TGC AAC TTC        336
Leu Gly Ile Phe Val Leu Leu Asp Tyr His Arg Ile Gly Cys Asn Phe
                100                 105                 110

ATA GAA CCC CTA TGG TAC ACC GAC AGC TTC TCG GAG CAG GAC TAC ATA        384
Ile Glu Pro Leu Trp Tyr Thr Asp Ser Phe Ser Glu Gln Asp Tyr Ile
            115                 120                 125

AAC ACC TGG GTT GAA GTC GCC CAG AGG TTC GGC AAG TAC TGG AAC GTT        432
Asn Thr Trp Val Glu Val Ala Gln Arg Phe Gly Lys Tyr Trp Asn Val
130                 135                 140

ATC GGC GCG GAC CTG AAG AAC GAA CCC CAC AGC TCA AGC CCC GCA CCT        480
Ile Gly Ala Asp Leu Lys Asn Glu Pro His Ser Ser Ser Pro Ala Pro
145                 150                 155                 160

GCC GCC TAC ACT GAC GGA AGT GGG GCC ACG TGG GGA ATG GGC AAC AAC        528
Ala Ala Tyr Thr Asp Gly Ser Gly Ala Thr Trp Gly Met Gly Asn Asn
                165                 170                 175

GCC ACC GAC TGG AAC CTG GCG GCT GAG AGG ATA GGA AGG GCA ATT CTG        576
Ala Thr Asp Trp Asn Leu Ala Ala Glu Arg Ile Gly Arg Ala Ile Leu
                180                 185                 190

GAG GTT GCC CCA CAA TGG GTT ATA TTT GTT GAG GGA ACC CAG TTC ACC        624
Glu Val Ala Pro Gln Trp Val Ile Phe Val Glu Gly Thr Gln Phe Thr
            195                 200                 205

ACC CCC GAG ATA GAC GGT AGG TAC AAG TGG GGC CAC AAC GCC TGG TGG        672
Thr Pro Glu Ile Asp Gly Arg Tyr Lys Trp Gly His Asn Ala Trp Trp
210                 215                 220

GGC GGA AAC CTT ATG GGT GTT AGG AAG TAC CCA GTT AAC CTG CCC AGG        720
Gly Gly Asn Leu Met Gly Val Arg Lys Tyr Pro Val Asn Leu Pro Arg
225                 230                 235                 240

GAC AAG GTT GTT TAC AGC CCC CAA GTT TAC GGT TCA GAA GTT TAC GAC        768
Asp Lys Val Val Tyr Ser Pro Gln Val Tyr Gly Ser Glu Val Tyr Asp
                245                 250                 255

CAG CCC TAC TTT GAC CCC GGT GAG GGG TTC CCC GAC AAC CTC CCC GAA        816
Gln Pro Tyr Phe Asp Pro Gly Glu Gly Phe Pro Asp Asn Leu Pro Glu
                260                 265                 270

ATA TGG TAC CAC CAC TTC GGC TAC GTA AAG CTT GAT CTC GGT TAC CCT        864
Ile Trp Tyr His His Phe Gly Tyr Val Lys Leu Asp Leu Gly Tyr Pro
            275                 280                 285

GTT GTT ATA GGT GAG TTC GGA GGC AAG TAC GGC CAT GGG GGA GAC CCG        912
Val Val Ile Gly Glu Phe Gly Gly Lys Tyr Gly His Gly Gly Asp Pro
290                 295                 300

AGG GAT GTC ACT TGG CAG AAC AAG ATA ATA GAC TGG ATG ATC CAG AAC        960
Arg Asp Val Thr Trp Gln Asn Lys Ile Ile Asp Trp Met Ile Gln Asn
305                 310                 315                 320

AAA TTC TGT GAC TTC TTC TAC TGG AGC TGG AAC CCA AAC AGC GGT GAC       1008
Lys Phe Cys Asp Phe Phe Tyr Trp Ser Trp Asn Pro Asn Ser Gly Asp
                325                 330                 335

ACC GGT GGA ATT CTG AAG GAT GAC TGG ACG ACA ATA TGG GAG GAC AAG       1056
Thr Gly Gly Ile Leu Lys Asp Asp Trp Thr Thr Ile Trp Glu Asp Lys
                340                 345                 350

TAC AAC AAC CTG AAG AGG CTC ATG GAC AGC TGT TCT GGA AAC GCC ACT       1104
Tyr Asn Asn Leu Lys Arg Leu Met Asp Ser Cys Ser Gly Asn Ala Thr
            355                 360                 365
```

-continued

```
GCC CCG TCC GTC CCC ACG ACA ACT ACA ACA ACA AGC ACA CCG CCA ACG      1152
Ala Pro Ser Val Pro Thr Thr Thr Thr Thr Thr Ser Thr Pro Pro Thr
    370                 375                 380

ACC ACA ACG ACT ACA ACA TCC ACT CCA ACG ACC ACT ACC CAG ACC CCG      1200
Thr Thr Thr Thr Thr Thr Ser Thr Pro Thr Thr Thr Thr Gln Thr Pro
385                 390                 395                 400

ACC ACC ACT ACT CCA ACT ACG ACA ACC ACC ACG ACC ACA ACT CCT TCA      1248
Thr Thr Thr Thr Pro Thr Thr Thr Thr Thr Thr Thr Thr Thr Pro Ser
                405                 410                 415

AAT AAC GTC CCA TTT GAA ATT GTG AAC GTT CTC CCG ACT AGC TCC CAG      1296
Asn Asn Val Pro Phe Glu Ile Val Asn Val Leu Pro Thr Ser Ser Gln
            420                 425                 430

TAC GAG GGA ACC AGC GTG GAG GTT GTA TGT GAT GGA ACC CAG TGT GCC      1344
Tyr Glu Gly Thr Ser Val Glu Val Val Cys Asp Gly Thr Gln Cys Ala
        435                 440                 445

TCC AGC GTT TGG GGA GCT CCG AAC CTC TGG GGA GTC GTT AAA ATC GGA      1392
Ser Ser Val Trp Gly Ala Pro Asn Leu Trp Gly Val Val Lys Ile Gly
    450                 455                 460

AAC GCC ACC ATG GAC CCC AAC GTT TGG GGC TGG GAG GAC GTT TAC AAG      1440
Asn Ala Thr Met Asp Pro Asn Val Trp Gly Trp Glu Asp Val Tyr Lys
465                 470                 475                 480

ACT GCA CCC CAG GAC ATT GGA ACC GGC AGC ACA AAG ATG GAG ATA AGG      1488
Thr Ala Pro Gln Asp Ile Gly Thr Gly Ser Thr Lys Met Glu Ile Arg
                485                 490                 495

AAC GGG GTG CTC AAG GTT ACA AAC CTC TGG AAC ATC AAC ATG CAT CCG      1536
Asn Gly Val Leu Lys Val Thr Asn Leu Trp Asn Ile Asn Met His Pro
            500                 505                 510

AAG TAT AAC ACA ATG GCA TAC CCG GAG GTC ATA TAC GGC GCC AAG CCT      1584
Lys Tyr Asn Thr Met Ala Tyr Pro Glu Val Ile Tyr Gly Ala Lys Pro
        515                 520                 525

TGG GGC AAC CAG CCA ATA AAC GCT CCG AAC TTC GTG CTC CCG ATA AAG      1632
Trp Gly Asn Gln Pro Ile Asn Ala Pro Asn Phe Val Leu Pro Ile Lys
    530                 535                 540

GTC TCC CAG CTT CCG AGG ATA CTT CGT TGA                              1662
Val Ser Gln Leu Pro Arg Ile Leu Arg
545                 550
```

(2) INFORMATION FOR SEQ ID NO: 2:

(i) SEQUENCE CHARACTERISTICS:
        (A) LENGTH: 553 AMINO ACIDS
        (B) TYPE: AMINO ACID
        (C) STRANDEDNESS: <Unknown>
        (D) TOPOLOGY: LINEAR (ii) MOLECULE TYPE: PROTEIN (xi) SEQUENCE DESCRIPTION: SEQ ID NO: 2:

```
Met Ile Asn Val Ala Thr Gly Glu Glu Thr Pro Ile His Leu Phe Gly
                5                   10                  15

Val Asn Trp Phe Gly Phe Glu Thr Pro Asn Tyr Val Val His Gly Leu
            20                  25                  30

Trp Ser Arg Asn Trp Glu Asp Met Leu Leu Gln Ile Lys Ser Leu Gly
        35                  40                  45

Phe Asn Ala Ile Arg Leu Pro Phe Cys Thr Gln Ser Val Lys Pro Gly
    50                  55                  60

Thr Met Pro Thr Ala Ile Asp Tyr Ala Lys Asn Pro Asp Leu Gln Gly
65                  70                  75                  80

Leu Asp Ser Val Gln Ile Met Glu Lys Ile Ile Lys Lys Ala Gly Asp
                85                  90                  95
```

```
Leu Gly Ile Phe Val Leu Leu Asp Tyr His Arg Ile Gly Cys Asn Phe
            100                 105                 110

Ile Glu Pro Leu Trp Tyr Thr Asp Ser Phe Ser Glu Gln Asp Tyr Ile
            115                 120                 125

Asn Thr Trp Val Glu Val Ala Gln Arg Phe Gly Lys Tyr Trp Asn Val
            130                 135                 140

Ile Gly Ala Asp Leu Lys Asn Glu Pro His Ser Ser Pro Ala Pro
145                 150                 155                 160

Ala Ala Tyr Thr Asp Gly Ser Gly Ala Thr Trp Gly Met Gly Asn Asn
                    165                 170                 175

Ala Thr Asp Trp Asn Leu Ala Ala Glu Arg Ile Gly Arg Ala Ile Leu
                180                 185                 190

Glu Val Ala Pro Gln Trp Val Ile Phe Val Glu Gly Thr Gln Phe Thr
            195                 200                 205

Thr Pro Glu Ile Asp Gly Arg Tyr Lys Trp Gly His Asn Ala Trp Trp
            210                 215                 220

Gly Gly Asn Leu Met Gly Val Arg Lys Tyr Pro Val Asn Leu Pro Arg
225                 230                 235                 240

Asp Lys Val Val Tyr Ser Pro Gln Val Tyr Gly Ser Glu Val Tyr Asp
                    245                 250                 255

Gln Pro Tyr Phe Asp Pro Gly Glu Gly Phe Pro Asp Asn Leu Pro Glu
                260                 265                 270

Ile Trp Tyr His His Phe Gly Tyr Val Lys Leu Asp Leu Gly Tyr Pro
            275                 280                 285

Val Val Ile Gly Glu Phe Gly Gly Lys Tyr Gly His Gly Gly Asp Pro
            290                 295                 300

Arg Asp Val Thr Trp Gln Asn Lys Ile Ile Asp Trp Met Ile Gln Asn
305                 310                 315                 320

Lys Phe Cys Asp Phe Phe Tyr Trp Ser Trp Asn Pro Asn Ser Gly Asp
                    325                 330                 335

Thr Gly Gly Ile Leu Lys Asp Asp Trp Thr Thr Ile Trp Glu Asp Lys
                340                 345                 350

Tyr Asn Asn Leu Lys Arg Leu Met Asp Ser Cys Ser Gly Asn Ala Thr
            355                 360                 365

Ala Pro Ser Val Pro Thr Thr Thr Thr Thr Ser Thr Pro Pro Thr
            370                 375                 380

Thr Thr Thr Thr Thr Thr Ser Thr Pro Thr Thr Thr Gln Thr Pro
385                 390                 395                 400

Thr Thr Thr Thr Pro Thr Thr Thr Thr Thr Thr Thr Pro Ser
                    405                 410                 415

Asn Asn Val Pro Phe Glu Ile Val Asn Val Leu Pro Thr Ser Ser Gln
                420                 425                 430

Tyr Glu Gly Thr Ser Val Glu Val Cys Asp Gly Thr Gln Cys Ala
            435                 440                 445

Ser Ser Val Trp Gly Ala Pro Asn Leu Trp Gly Val Val Lys Ile Gly
450                 455                 460

Asn Ala Thr Met Asp Pro Asn Val Trp Gly Trp Glu Asp Val Tyr Lys
465                 470                 475                 480

Thr Ala Pro Gln Asp Ile Gly Thr Gly Ser Thr Lys Met Glu Ile Arg
                    485                 490                 495

Asn Gly Val Leu Lys Val Thr Asn Leu Trp Asn Ile Asn Met His Pro
                500                 505                 510

Lys Tyr Asn Thr Met Ala Tyr Pro Glu Val Ile Tyr Gly Ala Lys Pro
```

```
                515                  520                 525
Trp Gly Asn Gln Pro Ile Asn Ala Pro Asn Phe Val Leu Pro Ile Lys
    530                 535                 540

Val Ser Gln Leu Pro Arg Ile Leu Arg
545                 550
```

(2) INFORMATION FOR SEQ ID NO: 3:

(i) SEQUENCE CHARACTERISTICS:
        (A) LENGTH: 46 NUCLEOTIDES
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO: 3:

```
AATAGCGGCC GCAAGCTTAT CGACGGTTTC CATATGGGGA TTGGTG                46
```

(2) INFORMATION FOR SEQ ID NO: 4:

(i) SEQUENCE CHARACTERISTICS:
        (A) LENGTH: 42 NUCLEOTIDES
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO: 4:

```
AATAGCGGCC GCGGATCCAG ACCAACTGGT AATGGTAGCG AC                    42
```

(2) INFORMATION FOR SEQ ID NO: 5:

(i) SEQUENCE CHARACTERISTICS:
        (A) LENGTH: 60 NUCLEOTIDES
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO: 5:

```
TTTATTCAAT TGATTAAAGA GGAGAAATTA ACTATGATAA ACGTTGCAAC GGGAGAGGAG  60
```

(2) INFORMATION FOR SEQ ID NO: 6:

(i) SEQUENCE CHARACTERISTICS:
        (A) LENGTH: 35 NUCLEOTIDES
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO: 6:

```
TTTATTGGAT CCTACTTTGT GTCAACGAAG TATCC                            35
```

ENDOGLUCANASES

This application is a divisional of application Ser. No. 09/066,544 filed on Apr. 24, 1998, now U.S. Pat. No. 6,001,984, which is a continuation application of U.S. application Ser. No. 08/651,572, filed May 22, 1996, now issued as U.S. Pat. No. 5,789,228, the entire contents of which are hereby incorporated by reference herein.

This invention relates to newly identified polynucleotides, polypeptides encoded by such polynucleotides, the use of such polynucleotides and polypeptides, as well as the production and isolation of such polynucleotides and polypeptides. More particularly, the polypeptide of the present invention has been putatively identified as an endoglucanase and in particular an enzyme having carboxymethyl cellulase activity.

Cellulose, a fibrous, tough, water-insoluble substance is found in the cell walls of plants, particularly, in stalks, stems, trunks and all the woody portions of plant tissues. Cellulose constitutes much of the mass of wood, and cotton is almost pure cellulose. Because cellulose is a linear, unbranched homopolysaccharide of 10,000 to 15,000 D-glucose units, it resembles amylose and the main chains of glycogen. But there is a very important difference, in cellulose, the glucose residues have the beta configuration, whereas in amylose, amylopectin and glycogen, the glucose is in the alpha configuration. The glucose residues in cellulose are linked by (beta 1→4) glycosidic bonds. This difference gives cellulose and amylose very different 3-dimensional structures and physical properties.

Cellulose cannot be used by most animals as a source of stored fuel, because the (beta 1→4) linkages of cellulose are not hydrolyzed by alpha-amylases. Termites readily digest cellulose but only because their intestinal tract harbors a symbiotic microorganism, *trichonympha*, which secretes cellulase, an enzyme that hydrolyses (beta 1→4) linkages between glucose units. The only vertebrates able to use cellulose as food are cattle and other ruminant animals (sheep, goats, camels and giraffes). The extra stomachs "rumens" of these animals teem with bacteria and protists that secrete cellulase.

The enzymatic hydrolysis of cellulose is considered to require the action of both endoglucanases (1,4-beta-D-glucan glucanohydrolase) and exoglucanases (1,4-beta-D-glucan cellobiohydrolase). A synergistic interaction of these enzymes is necessary for the complete hydrolysis of crystalline cellulose. (Caughlin, M. P., Genet. Eng. Rev., 3:39–109 (1985)). For the complete degradation of cellulose (cellulose to glucose), β-glucosidase might be required if the "exo" enzyme does not release glucose. 1,4-β-D-glucan glucohydrolase is another type of "exo" cellulase.

Thermophilic bacteria have received considerable attention as sources of highly active and thermostable cellulolytic and xylanolytic enzymes (Bronneomeier, K. and Staudenbauer, W. L., D. R. Woods (Ed.), The Clostridia and Biotechnology, Butterworth Publishers, Stoneham, Mass. (1993). Recently, the most extremely thermophilic organotrophic eubacteria presently known have been isolated and characterized. These bacteria, which belong to the genus *thermotoga*, are fermentative microorganisms metabolizing a variety of carbohydrates (Huber, R. and Stetter, K. O., in Ballows, et al., (Ed.), The Procaryotes, 2nd Ed., Springer-Verlaz, New York, pgs. 3809–3819 (1992)).

In Huber et al., 1986, Arch. Microbiol. 144:324–333, the isolation of the bacterium *Thermotoga maritima* is described. *T. maritima* is a eubacterium that is strictly anaerobic, rod-shaped, fermentative, hyperthermophilic, and grows between 55° C. and 90° C., with an optimum growth temperature of about 80° C. This eubacterium has been isolated from geothermally heated sea floors in Italy and the Azores. *T. maritima* cells have a sheath-like structure and monotrichous flagellation. *T. maritima* is classified in the eubacterium kingdom by virtue of having murein and fatty acid-containing lipids, diphtheria-toxin-resistant elongation factor 2, an RNA polymerase subunit pattern, and sensitivity to antibiotics.

Because to date most organisms identified from the archaeal domain are thermophiles or hyperthermophiles, archaeal bacteria are also considered a fertile source of thermophilic enzymes.

The polynucleotide and polypeptide encoded thereby of the present invention has been putatively identified as an endoglucanase enzyme having carboxymethyl cellulase activity.

In accordance with one aspect of the present invention, there is provided a novel enzyme, as well as active fragments, analogs and derivatives thereof.

In accordance with another aspect of the present invention, there are provided isolated nucleic acid molecules encoding an enzyme of the present invention including mRNAs, DNAs, cDNAs, genomic DNAs as well as active analogs and fragments of such enzymes.

In accordance with another aspect of the present invention there are provided isolated nucleic acid molecules encoding mature polypeptides expressed by the DNA contained in ATCC Deposit No. 97516.

In accordance with yet a further aspect of the present invention, there is provided a process for producing such polypeptide by recombinant techniques comprising culturing recombinant prokaryotic and/or eukaryotic host cells, containing a nucleic acid sequence encoding an enzyme of the present invention, under conditions promoting expression of said enzyme and subsequent recovery of said enzyme.

In accordance with yet a further aspect of the present invention, there is provided a process for utilizing such enzyme, or polynucleotide encoding such enzyme for degradation of cellulose for the conversion of plant biomass into fuels and chemicals, for use in detergents, the textile industry, in animal feed, in waste treatment, and in the fruit juice/brewing industry for the clarification and extraction of juices.

In accordance with yet a further aspect of the present invention, there is also provided nucleic acid probes comprising nucleic acid molecules of sufficient length to specifically hybridize to a nucleic acid sequence of the present invention.

In accordance with yet a further aspect of the present invention, there is provided a process for utilizing such enzymes, or polynucleotides encoding such enzymes, for in vitro purposes related to scientific research, for example, to generate probes for identifying similar sequences which might encode similar enzymes from other organisms.

These and other aspects of the present invention should be apparent to those skilled in the art from the teachings herein.

The following drawings are illustrative of embodiments of the invention and are not meant to limit the scope of the invention as encompassed by the claims.

FIGS. 1A, 1B is an illustration of the full-length DNA and corresponding deduced amino acid sequence of the enzyme of the present invention. Sequencing was performed using a 378 automated DNA sequencer (Applied Biosystems, Inc.).

The term "gene" means the segment of DNA involved in producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

"Recombinant" enzymes refer to enzymes produced by recombinant DNA techniques; i.e., produced from cells transformed by an exogenous DNA construct encoding the desired enzyme. "Synthetic" enzymes are those prepared by chemical synthesis.

A DNA "coding sequence of" or a "nucleotide sequence encoding" a particular enzyme, is a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The present invention provides a purified thermostable enzyme that catalyzes the hydrolysis of the beta 1,4 glycosidic bonds in cellulose to thereby degrade cellulose. The purified enzyme is an endoglucanase derived from an organism referred herein as "AEPII1a" which is a thermophilic archaeal bacteria which has a very high temperature optimum. The organism is strictly anaerobic, rod-shaped and fermentative, and grows between 55 and 90° C. (optimally at 85° C.). AEPII1a was discovered in a shallow marine hydrothermal area in Vulcano, Italy. The organism has coccoid cells occurring in singlets or pairs. AEPII1a grows optimally at 85° C. and pH 6.5 in a marine medium with cellulose as a substrate and nitrogen in gas phase.

The polynucleotide of this invention was originally recovered from a genomic gene library derived from AEPII1a as described below. It contains an open reading frame encoding a protein of 553 amino acid residues.

In a preferred embodiment, the endoglucanase enzyme of the present invention has a molecular weight of about 60.9 kilodaltons as measured by SDS-PAGE gel electrophoresis and an inferred molecular weight from the nucleotide sequence of the gene. This purified enzyme may be used to catalyze the enzymatic degradation of cellulose where desired. The endoglucanase enzyme of the present invention has a very high thermostability and has the closest homology to endo-1,4-beta-glucanase from *Xanthomonas campestris* with 50% identity and 71% similarity at the amino acid level.

In accordance with an aspect of the present invention, there are provided isolated nucleic acid molecules (polynucleotides) which encode for the mature enzyme having the deduced amino acid sequence of FIG. 1 (SEQ ID NO:2).

In accordance with another aspect of the present invention, there is provided an isolated polynucleotide encoding the enzyme of the present invention which has been deposited with an appropriate depository for the deposit of biological material. The deposited material is a pQET (Qiagen, Inc.) plasmid comprising the DNA of FIG. 1. The deposit has been deposited with the American Type Culture Collection, 12301 Parklawn Drive, Rockville, Md. 20852, USA, on Apr. 22, 1996 and assigned ATCC Deposit No. 97516.

The deposit has been made under the terms of the Budapest Treaty on the International Recognition of the deposit of micro-organisms for purposes of patent procedure. The strain will be irrevocably and without restriction or condition released to the public upon the issuance of a patent. The deposit is provided merely as convenience to those of skill in the art and are not an admission that a deposit be required under 35 U.S.C. §112. The sequences of the polynucleotides contained in the deposited materials, as well as the amino acid sequences of the polypeptides encoded thereby, are controlling in the event of any conflict with any description of sequences herein. A license may be required to make, use or sell the deposited materials, and no such license is hereby granted.

This invention, in addition to the isolated nucleic acid molecule encoding an endoglucanase enzyme disclosed in FIG. 1 (SEQ ID NO:1), also provides substantially similar sequences. Isolated nucleic acid sequences are substantially similar if: (i) they are capable of hybridizing under stringent conditions, hereinafter described, to SEQ ID NO:1; or (ii) they encode DNA sequences which are degenerate to SEQ ID NO:1. Degenerate DNA sequences encode the amino acid sequence of SEQ ID NO:2, but have variations in the nucleotide coding sequences. As used herein, "substantially similar" refers to the sequences having similar identity to the sequences of the instant invention. The nucleotide sequences that are substantially similar can be identified by hybridization or by sequence comparison. Enzyme sequences that are substantially similar can be identified by one or more of the following: proteolytic digestion, gel electrophoresis and/or microsequencing.

One means for isolating a nucleic acid molecule encoding an endoglucanase enzyme is to probe a genomic gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992). It is appreciated to one skilled in the art that SEQ ID NO:1, or fragments thereof (comprising at least 15 contiguous nucleotides), is a particularly useful probe. Other particular useful probes for this purpose are hybridizable fragments to the sequences of SEQ ID NO: 1 (i.e., comprising at least 15 contiguous nucleotides).

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acid is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardt's, and 0.5 mg/mL polyriboadenylic acid. Approximately $2 \times 10^7$ cpm (specific activity $4-9 \times 10^8$ cpm/ug)$^{32}$ of P end-labeled oligonucleotide probe are then added to the solution. After 12–16 hours of incubation, the membrane is washed for 30 minutes at room temperature in 1×SET (150 mM NaCl, 20 mM Tris hydrochloride, pH 7.8, 1 mM Na$_2$EDTA) containing 0.5% SDS, followed by a 30 minute wash in fresh 1×SET at Tm-10° C. for the oligo-nucleotide probe. The membrane is then exposed to auto-radiographic film for detection of hybridization signals.

Stringent conditions means hybridization will occur only if there is at least 90% identity, preferably at least 95% identity and most preferably at least 97% identity between the sequences. See J. Sambrook et al., Molecular Cloning, A Laboratory Manual (2d Ed. 1989) (Cold Spring Harbor Laboratory) which is hereby incorporated by reference in its entirety.

"Identity" as the term is used herein, refers to a polynucleotide sequence which comprises a percentage of the same bases as a reference polynucleotide (SEQ ID NO:1). For example, a polynucleotide which is at least 90% identical to a reference polynucleotide, has polynucleotide bases which are identical in 90% of the bases which make up the reference polynucleotide and may have different bases in 10% of the bases which comprise that polynucleotide sequence.

The present invention also relates to polynucleotides which differ from the reference polynucleotide such that the changes are silent changes, for example the changes do not alter the amino acid sequence encoded by the polynucleotide. The present invention also relates to nucleotide changes which result in amino acid substitutions, additions, deletions, fusions and truncations in the enzyme encoded by the reference polynucleotide (SEQ ID NO:1). In a preferred aspect of the invention these enzymes retain the same biological action as the enzyme encoded by the reference polynucleotide.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other animal sources or to screen such sources for related sequences.

The coding sequence for the endoglucanase enzyme of the present invention was identified by preparing an AEPII1a genomic DNA library and screening the library for the clones having endoglucanase activity. Such methods for constructing a genomic gene library are well-known in the art. One means, for example, comprises shearing DNA isolated from AEPII1a by physical disruption. A small amount of the sheared DNA is checked on an agarose gel to verify that the majority of the DNA is in the desired size range (approximately 3–6 kb). The DNA is then blunt ended using Mung Bean Nuclease, incubated at 37° C. and phenol/chloroform extracted. The DNA is then methylated using Eco RI Methylase. Eco RI linkers are then ligated to the blunt ends through the use of T4 DNA ligase and incubation at 4° C. The ligation reaction is then terminated and the DNA is cut-back with Eco RI restriction enzyme. The DNA is then size fractionated on a sucrose gradient following procedures known in the art, for example, Maniatis, T., et al., *Molecular Cloning*, Cold Spring Harbor Press, New York, 1982, which is hereby incorporated by reference in its entirety.

A plate assay is then performed to get an approximate concentration of the DNA. Ligation reactions are then performed and 1 μl of the ligation reaction is packaged to construct a library. Packaging, for example, may occur through the use of purified λgt11 phage arms cut with EcoRI and DNA cut with EcoRI after attaching EcoRI linkers. The DNA and λgt11 arms are ligated with DNA ligase. The ligated DNA is then packaged into infectious phage particles. The packaged phages are used to infect *E. coli* cultures and the infected cells are spread on agar plates to yield plates carrying thousands of individual phage plaques. The library is then amplified.

In a preferred embodiment, the enzyme of the present invention, was isolated from an AEPII1a library by the following technique:

1. λgt11 AEPII1a library was plated onto 6 LB/GelRite/0.1% CMC/NZY agar plates (~4,800 plaque forming units/plate) in *E.coli* Y1090 host with LB agarose containing 1 mM IPTG as top agarose. The plates were incubated at 37° C. overnight.

2. Plates were chilled at 4° C. for one hour.

3. The plates were overlayed with Duralon membranes (Stratagene) at room temperature for one hour and the membranes were oriented and lifted off the plates and stored at 4° C.

4. The top agarose layer was removed and plates were incubated at 72° C. for ~3 hours.

5. The plate surface was rinsed with NaCl.

6. The plate was stained with 0.1% Congo Red for 15 minutes.

7. The plate was destained with 1M NaCl.

8. The putative positives identified on plate were isolated from the Duralon membrane (positives are identified by clearing zones around clones). The phage was eluted from the membrane by incubating in 500 μl SM+25 μl CHCl$_3$ to elute.

9. Insert DNA was subcloned into pBluescript II SK(+) cloning vector (Stratagene), and subclones were reassayed for CMCase activity using the following protocol:

i) Spin 1 ml overnight miniprep of clone at maximum speed for 3 minutes.

ii) Decant the supernatant and use it to fill "wells" that have been made in an LB/GelRite/0.1% CMC plate.

iii) Incubate at 72° C. for 2 hours.

iv) Stain with 0.1% Congo Red for 15 minutes.

v) Destain with 1M NaCl for 15 minutes.

vi) Identify positives by clearing zone around clone.

Fragments of the full length gene of the present invention may be used as a hybridization probe for a cDNA or a genomic library to isolate the full length DNA and to isolate other DNAs which have a high sequence similarity to the gene or similar biological activity. Probes of this type have at least 10, preferably at least 15, and even more preferably at least 30 bases and may contain, for example, at least 50 or more bases. The probe may also be used to identify a DNA clone corresponding to a full length transcript and a genomic clone or clones that contain the complete gene including regulatory and promotor regions, exons, and introns.

The isolated nucleic acid sequences and other enzymes may then be measured for retention of biological activity characteristic to the enzyme of the present invention, for example, in an assay for detecting enzymatic endoglucanase activity. Such enzymes include truncated forms of endoglucanase, and variants such as deletion and insertion variants.

Examples of such assays include an assay for the detection of endoglucanase activity based on specific interaction of direct dyes such as Congo red with polysaccharides. This colorant reacts with beta-1,4-glucans causing a visible red shift (Wood, P. J., Carbohydr. Res., 85:271 (1980) and Wood, P. J., Carbohydr. Res., 94:c19 (1981)). The preferred substrate for the test is carboxymethylcellulose (CMC) which can be obtained from different sources (Hercules Inc., Wilmington, DE, Type 4M6F or Sigma Chemical Company, St. Louis, Mo., Medium Viscosity). The CMC is incorporated as the main carbon sources into a minimal agar medium in quantities of 0.1–1.0%. The microorganisms can be screened directly on these plates, but the replica plating technique from a master plate is preferable since the visualization of the activity requires successive flooding with the reagents, which would render the reisolation of active colonies difficult. Such endoglucanase-producing colonies are detectable after a suitable incubation time (1–3 days depending on the growth), by flooding the plate with 10 ml of a 0.1% aqueous solution of Congo Red. The coloration is terminated after 20 minutes by pouring off the dye and flooding the plates with 10 ml of 5M NaCl solution (commercial salt can be used). After an additional 20 minutes, the salt solution is discarded and endoglucanase activity is revealed by a pale-orange zone around the active microorganisms. In some cases, these zones can be enhanced by treating the plates with 1 N acetic acid, causing the dye to change its color to blue.

The same technique can be used as a cup-plate diffusion assay with excellent sensitivity for the determination of endoglucanase activity in culture filtrates or during enzyme purification steps (Carger, J. H., Anal. Biochem., 153:75 (1986)). See generally, Methods for Measuring Cellulase Activities, Methods in Enzymology, Vol. 160, pgs. 87–116.

The enzyme of the present invention has enzymatic activity with respect to the hydrolysis of the beta 1,4 glycosidic bonds in carboxymethylcellulose, since the halos discussed above are shown around the colonies.

The polynucleotide of the present invention may be in the form of DNA which DNA includes cDNA, genomic DNA, and synthetic DNA. The DNA may be double-stranded or single-stranded, and if single stranded may be the coding strand or non-coding (anti-sense) strand. The coding sequence which encodes the mature enzyme may be identical to the coding sequence shown in FIG. 1 (SEQ ID NO:1) and/or that of the deposited clone or may be a different coding sequence which coding sequence, as a result of the redundancy or degeneracy of the genetic code, encodes the same mature enzyme as the DNA of FIG. 1 (SEQ ID NO:1).

The polynucleotide which encodes for the mature enzyme of FIG. 1 (SEQ ID NO:2) may include, but is not limited to: only the coding sequence for the mature enzyme; the coding sequence for the mature enzyme and additional coding sequence such as a leader sequence or a proprotein sequence; the coding sequence for the mature enzyme (and optionally additional coding sequence) and non-coding sequence, such as introns or non-coding sequence 5' and/or 3' of the coding sequence for the mature enzyme.

Thus, the term "polynucleotide encoding an enzyme (protein)" encompasses a polynucleotide which includes only coding sequence for the enzyme as well as a polynucleotide which includes additional coding and/or non-coding sequence.

The present invention further relates to variants of the hereinabove described polynucleotides which encode for fragments, analogs and derivatives of the enzyme having the deduced amino acid sequence of FIG. 1 (SEQ ID NO:2). The variant of the polynucleotide may be a naturally occurring allelic variant of the polynucleotide or a non-naturally occurring variant of the polynucleotide.

Thus, the present invention includes polynucleotides encoding the same mature enzyme as shown in FIG. 1 (SEQ ID NO:2) as well as variants of such polynucleotides which variants encode for a fragment, derivative or analog of the enzyme of FIG. 1 (SEQ ID NO:2). Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1). As known in the art, an allelic variant is an alternate form of a polynucleotide sequence which may have a substitution, deletion or addition of one or more nucleotides, which does not substantially alter the function of the encoded enzyme.

The present invention also includes polynucleotides, wherein the coding sequence for the mature enzyme may be fused in the same reading frame to a polynucleotide sequence which aids in expression and secretion of an enzyme from a host cell, for example, a leader sequence which functions to control transport of an enzyme from the cell. The enzyme having a leader sequence is a preprotein and may have the leader sequence cleaved by the host cell to form the mature form of the enzyme. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature enzyme, or for an enzyme having a prosequence or for an enzyme having both a prosequence and a presequence (leader sequence).

present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode enzymes which either retain substantially the same biological function or activity as the mature enzyme encoded by the DNA of FIG. 1 (SEQ ID NO:1).

Alternatively, the polynucleotide may have at least 15 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a PCR primer.

Thus, the present invention is directed to polynucleotides having at least a 70% identity, preferably at least 90% identity and more preferably at least a 95% identity to a polynucleotide which encodes the enzyme of SEQ ID NO:2 as well as fragments thereof, which fragments have at least 30 bases and preferably at least 50 bases and to enzymes encoded by such polynucleotides.

The present invention further relates to a enzyme which has the deduced amino acid sequence of FIG. 1 (SEQ ID NO:2), as well as fragments, analogs and derivatives of such enzyme.

The terms "fragment," "derivative" and "analog" when referring to the enzyme of FIG. 1 (SEQ ID NO:2) means a enzyme which retains essentially the same biological function or activity as such enzyme. Thus, an analog includes a proprotein which can be activated by cleavage of the proprotein portion to produce an active mature enzyme.

The enzyme of the present invention may be a recombinant enzyme, a natural enzyme or a synthetic enzyme, preferably a recombinant enzyme.

The fragment, derivative or analog of the enzyme of FIG. 1 (SEQ ID NO:2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature enzyme is fused with another compound, such as a compound to increase the half-life of the enzyme (for example, polyethylene glycol), or (iv) one in which the additional amino acids are fused to the mature enzyme, such as a leader or secretory sequence or a sequence which is employed for purification of the mature enzyme or a proprotein sequence. Such fragments, derivatives and analogs are deemed to be within the scope of those skilled in the art from the teachings herein.

The enzymes and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

The enzymes of the present invention include the enzyme of SEQ ID NO:2 (in particular the mature enzyme) as well as enzymes which have at least 70% similarity (preferably at least 70% identity) to the enzyme of SEQ ID NO:2 and more preferably at least 90% similarity (more preferably at least 90% identity) to the enzyme of SEQ ID NO:2 and still more preferably at least 95% similarity (still more preferably at least 95% identity) to the enzyme of SEQ ID NO:2 and also include portions of such enzymes with such portion of the enzyme generally containing at least 30 amino acids and more preferably at least 50 amino acids.

As known in the art "similarity" between two enzymes is determined by comparing the amino acid sequence and its conserved amino acid substitutes of one enzyme to the sequence of a second enzyme. Similarity may be determined by procedures which are well-known in the art, for example, a BLAST program (Basic Local Alignment Search Tool at the National Center for Biological Information).

A variant, i.e. a "fragment", "analog" or "derivative" enzyme, and reference enzyme may differ in amino acid sequence by one or more substitutions, additions, deletions, fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Most highly preferred are variants which retain the same biological function and activity as the reference polypeptide from which it varies.

Fragments or portions of the enzymes of the present invention may be employed for producing the corresponding full-length enzyme by peptide synthesis; therefore, the fragments may be employed as intermediates for producing the full-length enzymes. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of enzymes of the invention by recombinant techniques.

Host cells are genetically engineered (transduced or transformed or transfected) with the vectors containing the polynucleotides of this invention. Such vectors may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing enzymes by recombinant techniques. Thus, for example, the polynucleotide may be included in any one of a variety of expression vectors for expressing an enzyme. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct MRNA synthesis. As representative examples of such promoters, there may be mentioned: LTR or SV40 promoter, the $E.$ $coli.$ lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli.$ The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Bacillus subtilis*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBluescript II (Stratagene); pTRC99a, pKK223-3, pDR540, pRIT2T (Pharmacia); Eukaryotic: pXT1, pSG5 (Stratagene) pSVK3, pBPV, pMSG, pSVLSV40 (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the enzymes of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, Cold Spring Harbor, N.Y., (1989), the disclosure of which is hereby incorporated by reference.

Transcription of the DNA encoding the enzymes of the present invention by higher eukaryotes is increased by inserting an enhancer sequence into the vector. Enhancers are cisacting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the enzymes of the present invention may be glycosylated or may be non-glycosylated. Enzymes of the invention may or may not also include an initial methionine amino acid residue.

The enzyme of this invention may be employed for any purpose in which such enzyme activity is necessary or desired. In a preferred embodiment the enzyme is employed for catalyzing the hydrolysis of cellulose. The degradation of cellulose may be used for the conversion of plant biomass into fuels and chemicals.

The enzyme of the present invention may also be employed in the detergent and textile industry, in the production of animal feed, in waste treatment and in the fruit juice/brewing industry for the clarification and extraction of juices.

In a preferred embodiment, the enzyme of the present invention is a thermostable enzyme which is stable to heat and is heat resistant and catalyzes the enzymatic hydrolysis of cellulose, i.e., the enzyme is able to renature and regain activity after a brief (i.e., 5 to 30 seconds), or longer period, for example, minutes or hours, exposure to temperatures of 80° C. to 105° C. and has a temperature optimum above 60° C.

The enzymes, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the enzymes corresponding to a sequence of the present invention can be obtained by direct injection of the enzymes into an animal or by administering the enzymes to an animal, preferably a nonhuman. The antibody so obtained will then bind the enzymes itself. In this manner, even a sequence encoding only a fragment of the enzymes can be used to generate antibodies binding the whole native enzymes. Such antibodies can then be used to isolate the enzyme from cells expressing that enzyme.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic enzyme products of this invention. Also, transgenic mice may be used to express humanized antibodies to immunogenic enzyme products of this invention.

Antibodies generated against the enzyme of the present invention may be used in screening for similar enzymes from other organisms and samples. Such screening techniques are known in the art, for example, one such screening assay is described in "Methods for Measuring Cellulase Activities", *Methods in Enzymology*, Vol 160, pp. 87–116, which is hereby incorporated by reference in its entirety. Antibodies may also be employed as a probe to screen gene libraries generated from this or other organisms to identify this or cross reactive activities.

The present invention is further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in the method of Sambrook, Fritsch and Maniatus, 1989.

EXAMPLE 1

Bacterial Expression and Purification of Endoglucanase

An AEPII1a genomic library was constructed in the Lambda gt11 cloning vector (Stratagene Cloning Systems). The library was screened in Y1090 E. coli cells (Stratagene) for endoglucanase activity and a positive clone was identified and isolated. DNA of this clone was used as a template in a 100 ul PCT reaction using the following primer sequences: 5' primer: AATAGCGGCCGCAAGCTTATC-GACGGTTTCCATATGGGGATTGGTG (SEQ ID NO:3). 3' primer: AATAGCGGCCGCGGATCCAGACCAACTGG TAATGGTAGCGAC (SEQ ID NO:4).

The PCR reaction product was purifed and digested with Not I restriction enzyme. The digested product was subcloned into the pBluescript II SK cloning vector (Stratagene) and sequenced. The sequence information was used in the generation of primer sequences which were subsequently used to PCR amplify the target gene encoding the endoglucanase. The primer sequences used were as follows:

5' primer: TTTATTCAATTGATTAAAGAGGAGAAAT-TAACTATGATAAACGTTGC AACGGGAGAGGAG (SEQ ID NO:5) and 3' primer: TTTATTGGATCCTACTTTGTGTCAAC-GAAGTATCC (SEQ ID NO:6).

The amplification product was digested with the restriction enzymes MfeI and BamHI. The digested product was then ligated to pQET cloning vector, a modified form of a pQE vector (Qiagen, Inc.) which was previously digested with BamHI and EcoRI compatible with MfeI. The pQE vector encodes antibiotic resistance ($Amp^r$), a bacterial origin of replication (ori), an IPTG-regulatable promoter operator (P/O), a ribosome binding site (RBS), a 6-His tag and restriction enzyme sites.

The amplified sequences were inserted in frame with the sequence encoding for the RBS. The ligation mixture was then used to transform the E. coli strain M15/pREP4 (Qiagen, Inc.) by electroporation. M15/pREP4 contains multiple copies of the plasmid pREP4, which expresses the lacI repressor and also confers kanamycin resistance ($Kan^r$). Positive recombinant transformants were identified as having thermostable CMCase/endoglucanase activity by the assay described above. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture was used to inoculate a large culture at a ratio of 1:100 to 1:250. The cells were grown to an optical density 600 ($O.D.^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation.

The primer sequences set out above may also be employed to isolate the target gene from the deposited material by hybridization techniques described above.

Numerous modifications and variations of the present invention are possible in light of the above teachings and, therefore, within the scope of the appended claims, the invention may be practiced otherwise than as particularly described.

What is claimed is:

1. A purified enzyme comprising:

an amino acid sequence which is at least 70% identical to the amino acid sequence set forth in SEQ ID NO:2 and which has endoglucanase activity.

2. The enzyme of claim 1, wherein said enzyme catalyzes the hydrolysis of the beta 1,4 glycosidic bond in cellulose.

3. An enzyme encoded by an isolated polynucleotide which is at least 70% identical to (a) a polynucleotide encoding an enzyme comprising amino acid 1 to amino acid 553 of SEQ ID NO:2 and having endogluconase activity; and (b) a polynucleotide which is complementary to the polynucleotide of (a).

4. An enzyme of claim 1 having an amino acid sequence identical to the amino acid sequence set forth SEQ ID NO:2 and conservative variations thereof.

5. An enzyme of claim 1, wherein the enzyme is at least 90% identical to the amino acid sequence set forth SEQ ID NO:2.

6. An enzyme of claim 1 having at least 30 contiguous amino acid residues of SEQ ID NO:2.

7. The enzyme of claim 3 wherein the polynucleotide encodes an enzyme having an amino acid sequence identical to the amino acid sequence set forth SEQ ID NO:2.

8. The enzyme of claim 3 wherein the polynucleotide encodes at least 30 contiguous amino acid residues of SEQ ID NO:2.

* * * * *